United States Patent
Shao et al.

(10) Patent No.: US 10,768,099 B2
(45) Date of Patent: Sep. 8, 2020

(54) IN-VITRO BIOLOGICAL VALVE CALCIFICATION EVALUATION METHOD AND REDUCING CALCIUM INGREDIENT SOLUTION

(71) Applicant: VENUS MEDTECH (HANGZHOU), INC., Hangzhou, Zhejiang (CN)

(72) Inventors: Nan Shao, Hangzhou (CN); Dajun Kuang, Hangzhou (CN)

(73) Assignee: VENUS MEDTECH (HANGZHOU) INC., Hangzhou (CN)

( * ) Notice: Subject to any disclaimer, the term of this patent is extended or adjusted under 35 U.S.C. 154(b) by 305 days.

(21) Appl. No.: 15/876,908

(22) Filed: Jan. 22, 2018

(65) Prior Publication Data
US 2018/0149585 A1 May 31, 2018

Related U.S. Application Data

(63) Continuation of application No. PCT/CN2016/000412, filed on Jul. 22, 2016.

(30) Foreign Application Priority Data

Jul. 22, 2015 (CN) .......................... 2015 1 0434781

(51) Int. Cl.
| | | |
|---|---|---|
| *G01N 21/31* | (2006.01) | |
| *G01N 1/28* | (2006.01) | |
| *A61F 2/24* | (2006.01) | |
| *A61L 27/36* | (2006.01) | |
| *G01N 27/30* | (2006.01) | |
| *G01N 1/38* | (2006.01) | |
| *G01N 21/00* | (2006.01) | |
| *G01N 1/44* | (2006.01) | |
| *G01N 1/40* | (2006.01) | |

(52) U.S. Cl.
CPC .......... *G01N 21/31* (2013.01); *A61F 2/2433* (2013.01); *A61L 27/3687* (2013.01); *G01N 1/28* (2013.01); *G01N 1/38* (2013.01); *G01N 21/00* (2013.01); *G01N 1/4044* (2013.01); *G01N 1/44* (2013.01); *G01N 21/3103* (2013.01); *G01N 27/30* (2013.01)

(58) Field of Classification Search
CPC .......... G01N 21/31; G01N 21/00; G01N 1/38; G01N 1/28; G01N 21/3103; G01N 1/4044; G01N 1/44; G01N 27/30; A61L 27/3687; A61F 2/2433
See application file for complete search history.

(56) References Cited

U.S. PATENT DOCUMENTS 4,976,733 A * 12/1990 Girardot ............. A61L 27/3687
427/417

FOREIGN PATENT DOCUMENTS

CN 104990882 A 10/2015

OTHER PUBLICATIONS

Wei Xu-feng et al, "In vitro calcium deposition of biovalve material treated by epoxy chloropropane", Jan. 2005, Chinese Journal of Clinical Rehabilitation.
Wei XuFeng, "Mechanism of Anticalcification of Bioprostheti Heart Valves Pretreated by Epoxy Chloropropan", May 2005, Department of cardiovascular sugery, xijing hospital, Fourth Military Medical University.

* cited by examiner

*Primary Examiner* — Benjamin R Whatley
*Assistant Examiner* — Jean Caraballo-Leon
(74) *Attorney, Agent, or Firm* — Stein IP, LLC

(57) ABSTRACT

An in-vitro biological valve calcification evaluation method, comprising the following steps: preparing calcification evaluation solution comprising glutaraldehyde solution, saline solution, borate buffer solution, reducing calcium ingredient solution and calcium-containing plasma solution, the reducing calcium ingredient solution comprising alcohol, alkaline solution, oil and its derivatives, and buffer solution; preheating the reducing calcium ingredient solution; conducting treatment with the glutaraldehyde solution prior to reducing calcium ingredient solution; conducting treatment with the reducing calcium ingredient solution; preserving the valve samples; conducting in-vitro calcification reaction with the calcium-containing plasma solution; and detecting calcium content by atomic absorption spectrum.

11 Claims, No Drawings

IN-VITRO BIOLOGICAL VALVE CALCIFICATION EVALUATION METHOD AND REDUCING CALCIUM INGREDIENT SOLUTION

CROSS-REFERENCE TO RELATED APPLICATIONS

This application is a bypass continuation of International Application No. PCT/CN2016/000412, filed Jul. 22, 2016, which claims the benefit of priority to Chinese Application No. 201510434781.X, filed Jul. 22, 2015, in the State Intellectual Property Office. All disclosures of the document(s) named above are incorporated herein in their entireties by reference.

TECHNICAL FIELD

The present invention relates to the field of biological valves, in particular to an in-vitro biological valve calcification evaluation method and reducing calcium ingredient solution.

BACKGROUND

Currently, among the elderly people over 65 years old, the occurrence of aortic valve stenosis caused by aortic valve calcification is up to 2%-7%, and the proportion of aortic valve stenosis increases with age. Patients with serious aortic stenosis suffer from serious left ventricular dysfunction, which results in bad life quality of the patients and significant shortened lifetime. Effective treatments are required.

For patients with severe aortic valve in surgery indications, surgical prosthetic aortic valve replacement (either mechanical valve or biological valve) is still the preferred treatment, the aortic valve orifice area can often reach to larger than 1.5 cm$^2$ after replacement. However, the incidence of deaths and other serious complications following surgical aortic valve replacement have been greatly increased in those patients who are elderly, with aortic stenosis at the final stage, or multiple systemic serious complications. Method of percutaneous balloon aortic valvuloplasty for the treatment of aortic stenosis in the elderly is no longer used for serious aortic stenosis due to high incidence of intraoperative and postoperative deaths, stroke, aortic rupture, serious aortic insufficiency and other serious complications, as well as occurrence of obvious stenosis of aortic valve in a short term (3-12 months) after the operation. In addition, it is very difficult in the clinical treatment for elderly patients with serious aortic stenosis but without surgical indications.

In the prior art, prior to the animal experiment, a pig or a sheep at a appropriate age is selected, surgical risk and match degree are evaluated after ultrasound examination and health observation by doctors, to determine the congruency of the diameter of the valve frame and the main pulmonary artery diameter, the size of the valve frame is required to match the caliber of the aorta or pulmonary artery to prevent paravalvular leakage or displacement and so on. Then animal clinical experiment is carried out according to animal clinical requirements, the treated biological valve is implanted into the body of the pig or the sheep, if the valve is observed by ultrasonography to work well upon feeding for an observation period of six months to one year, the biological valve is removed by anatomizing and the calcium content in biological valve tissue is detected by atom absorption spectroscopy to determine the anti-calcification properties of the biological valve.

There are some limitations to evaluate the biological valve calcification through animal clinical experiment, the high technical dependence on clinical surgeries and clinician's technique, the corresponding requirements to selection of animals, and other symptoms such as biological valve epidermidalization, growth of neoplasm etc. may occur due to long feeding period, feeding environment effects and individual differences, and cannot accurately and effectively reflect the chemical action of biological valve after chemical reaction with calcium ions. The existing methods not only increase the technical difficulty but also greatly increase the time and cost, meanwhile, the evaluation of the calcification performance of the biological valve is interfered by many factors.

SUMMARY

The technical problem to be solved in the present invention is to provide a method for in-vitro biological valve calcification evaluation against the above defects in the prior art, which greatly shortens the period for evaluating the calcification and is an efficient standardized evaluation method.

Another technical problem to be solved by the present invention is to provide an reducing calcium ingredient solution which can reduce the binding force between the biological valve and calcium ions by chemical treatment of the biological valve thereby blocking certain free chemical groups, thus reducing the calcium content of the biological valve, and enhancing the anti-calcification capacity of the biological valve. The f term Reducing Calcium Ingredient is referred to as RCI hereinafter.

The technical solution adopted by the present invention to solve the technical problem is to provide an in-vitro biological valve calcification evaluation method, which comprises the following steps:

(1) preparing calcification evaluation solution; the calcification evaluation solution comprising: glutaraldehyde solution, saline solution, borate buffer solution, reducing calcium ingredient solution and calcium-containing plasma solution, the reducing calcium ingredient solution comprising alcohol, alkaline solution, oil and its derivatives, and buffer solution;

(2) preheating the reducing calcium ingredient solution: placing the reducing calcium ingredient solution in 30-40° C. thermostat water bath;

(3) conducting treatment prior to reducing calcium ingredient solution: taking a valve sample and soaking the valve sample in the glutaraldehyde solution completely, standing at room temperature;

(4) conducting treatment with the reducing calcium ingredient solution: removing the glutaraldehyde solution, and adding the borate buffer solution to immerse the sample therein, then removing the borate buffer solution, and soaking the sample in the reducing calcium ingredient solution completely within a 30-40° C. thermostat water bath;

(5) preserving the valve samples: removing the reducing calcium ingredient solution from the container, adding the saline solution until the valve sample is completely soaked, and keeping the sample;

(6) conducting in-vitro calcification reaction: putting the valve sample into the calcium-containing plasma solution in 30-40° C. thermostat water bath for a period of any days within 60 days to let the valve sample fully react with quantitative calcium ions of the solution, such that calcium ions are bonded to the valve sample by chemical bonding;

(7) detecting calcium content: measuring the calcium content of the reacted valve sample by atomic absorption spectrum to evaluate the calcium content of the valve sample, and comparing it with a standard sample.

Preferably, the concentration of the glutaraldehyde solution is 0.25-5.0%, the compositions and contents of each 5 L volume of the glutaraldehyde solution comprising: magnesium sulfate 1.0-3.0 g; potassium chloride 1.0-3.0 g; disodium hydrogen phosphate 3.0-5.0 g; potassium dihydrogen phosphate 0.6-1.2 g; sodium chloride 15-30 g; 25% glutaraldehyde 150-250 ml; isopropanol 500-1000 ml; and adding pure water to make the whole volume to 5 L.

Preferably, the concentration of the saline solution is 0.9%, the compositions and contents of each 10 L volume of the saline solution comprising: sodium chloride 90 g±0.1 g; and adding pure water to make the whole volume to 10 L.

Preferably, the compositions and contents of each 1 L volume of the borate buffer solution comprises: sodium chloride 3.0-15.0 g; sodium tetraborate 2.0-5.0 g; and adding pure water to make the whole volume to 1 L, with a pH of 8.5-9.5.

Preferably, wherein the compositions and contents of each 1 L volume of the reducing calcium ingredient solution comprises: reagent A 150-300 ml, wherein the reagent A is alcohol; reagent B 10-100 ml, wherein the reagent B is alkaline solution; reagent C 0.5-9.0 g, wherein the reagent C is oil or its derivative; reagent D 690~820 ml with a pH of 8.5-9.5, wherein the reagent D is buffer solution.

Preferably, the plasma is plasma substitute, the compositions and contents of each 1 L volume of the plasma comprising: 10% $CaCl_2$ solution 10-15 ml; and hydroxyethyl starch 20 sodium chloride injection 900-1000 ml.

Preferably, the reagent A comprises any one of ethanol, isopropanol, and amyl alcohol.

Preferably, the reagent B comprises KOH or NaOH.

Preferably, the reagent C comprises one or more of tetraenoic acid, linoleic acid, eicosatrienoic acid, linolenic acid, aminoleic acid, diacid, heptanoic acid, palmitic acid, stearic acid, oleic acid, and derivatives thereof.

Preferably, the reagent D is buffer solution comprising phosphate buffer solution, borate buffer solution or glycine hydrochloride buffer solution.

Another aspect of the present invention is to provide an anti-calcification factor solution, comprising: reagent A, reagent B, reagent C, and reagent D, wherein:

reagent A is alcohol, comprising any one of ethanol, isopropanol and amyl alcohol;

reagent B is alkaline solution, comprising KOH or NaOH;

reagent C is oil and its derivatives, comprising one or more of tetraenoic acid, linoleic acid, eicosatrienoic acid, linolenic acid, aminoleic acid, lauric acid, heptanoic acid, palmitic acid, stearic acid, and derivatives thereof;

reagent D is buffer solution, comprising phosphate buffer, borate buffer or glycine hydrochloride buffer with a pH of 8.5-9.

The beneficial effects of the present invention are as follows: the method for in-vitro biological valve calcification evaluation of the present invention has a short evaluation period, and in the meanwhile reduces the procedures, saves the cost of evaluation; the biological valve is treated chemically by the coordination of the anti-calcification factor solution, to block certain free chemical groups, reduce the binding force between the biological valve and calcium ions, thus reducing the calcium content of the biological valve, and enhancing the anti-calcification capacity of the biological valve; it can rapidly and effectively estimate the biological valve anti-calcification performance after a chemical treatment by the in-vitro biological valve evaluation method according to the present invention.

DETAILED DESCRIPTION

The preferred embodiments of the present invention are described in detail below.

The specific solution is as follows.

1. Preparing calcification evaluation solution.

Five kinds of solution are required in the present invention, i.e., 0.25-5.0% glutaraldehyde solution, 0.9% saline solution, BBS solution, RCI solution, calcium-containing plasma substitute solution. The respective compositions and contents thereof are shown as follows.

| 0.25-5.0% glutaraldehyde solution | |
|---|---|
| Composition | Content/5 L |
| Magnesium sulfate | 1.0-3.0 g |
| Potassium chloride | 1.0-3.0 g |
| Disodium hydrogen phosphate | 3.0-5.0 g |
| Potassium dihydrogen phosphate | 0.6-1.2 g |
| Sodium chloride | 15.0-30.0 g |
| 25% glutaraldehyde | 150-250 ml |
| Isopropanol | 500-1000 ml |
| Pure water | Add to 5 L |

| 0.9% saline solution | |
|---|---|
| Composition | Content/10 L |
| Sodium chloride | 90 g ± 0.1 g |
| Pure water | Add to 10 L |

| Borate buffer solution (BBS) | |
|---|---|
| Composition | Content/1 L |
| Sodium chloride | 3.0-15.0 g |
| Sodium tetraborate | 2.0-5.0 g |
| Pure water | Add to 1 L |

| Reducing calcium ingredient(RCI) solution | |
|---|---|
| Composition | Content/1 L |
| Reagent A | 150-300 ml |
| Reagent B | 10-100 ml |
| Reagent C | 0.5-9.0 g |
| Solution D | 690-820 ml |

Among the above reagents:

reagent A is alcohol, comprising any one of ethanol, isopropanol and amyl alcohol;

reagent B is alkaline solution, comprising either KOH or NaOH;

reagent C is oil or its derivatives, comprising one or more of the following: tetraenoic acid, linoleic acid, eicosatrienoic acid, linolenic acid, amino oleic acid, lauric acid, heptanoic acid, palmitic acid, stearic acid, oleic acid, and derivatives thereof;

reagent D is buffer solution, comprising any one of phosphate buffer solution, borate buffer solution and glycine hydrochloride buffer solution, with a pH of 8.5-9.

| Calcium-containing plasma substitute solution | |
|---|---|
| Composition | Content/1L |
| 10% $CaCl_2$ solution | 10-15 ml |
| Hydroxyethyl starch 20 sodium chloride injection | 900-1000 ml |

2. Pre-Heating RCI Solution.

Place the RCI solution in 30-40° C. thermostat water bath for 18-24 h at a rotating speed of 5-10 rpm.

This process is mainly for preheating RCI solution, so that the active ingredients are fully uniform, to obtain a stable and effective solution for use.

3. Treatment Prior to Reducing Calcium Ingredient (PRCI).

Take valve samples, and put them into an empty container, completely soak the samples with the glutaraldehyde solution, standing for 18-24 h at room temperature.

This process is to achieve saturated cross-linking and sufficient matched functional groups of valve by soaking the valve in glutaraldehyde solution.

4. RCI Treatment.

Remove the liquid, add BBS to immerse the samples therein, clean the samples with shaking once or several times, then remove the liquid, and soak the samples in the RCI solution completely, within a 30-40° C. thermostat water bath for 67-72 h at a rotating speed of 120-130 rpm.

This process is to make the chemicals in the RCI solution chemically bond the free groups in the valve samples, to block the free aldehyde groups and carboxyl groups in the valve.

5. Valve Samples Storage.

Remove the lipid, and add 0.9% saline solution to completely soak the samples, and keep them at a temperature of 2-8° C.

6. In-Vitro Calcification Reaction.

Put the samples into the calcium-containing plasma substitute solution, thermostat water bath for a period of 10 days, 15 days, 30 days, and 60 days respectively, at a temperature of 30-40° C., 120 rpm.

This process is an important step of evaluating the anti-calcification performance of the biological valves. The biological valves are reacted with a quantitative calcium solution sufficiently and the calcium ions are chemically bonded to the valves to evaluate the content of calcium attached to the valves.

7. Detection of Calcium Content.

The samples preserved for 0, 10, 15, 30 and 60 days were respectively taken for calcium content determination by means of atomic absorption spectrum.

| Results of calcium content detection | | |
|---|---|---|
| Days | Control samples mg/100 g | Anti-calcification samples mg/100 g |
| 0 | 13.04 | 15.25 |
| 10 | 31.37 | 20.36 |
| 15 | 48.38 | 26.83 |
| 30 | 98.03 | 60.59 |
| 60 | 236.95 | 79.20 |

As can be seen from the results of the above table, the calcium content of the samples after RCI processing is lower than that of the control samples, and the evaluation method is shown to be effective.

Examples 1-4

1. Prepare Calcification Evaluation Solution.

Five kinds of solution are required in the present invention, i.e., 0.25-5.0% glutaraldehyde solution, 0.9% saline solution, BBS solution, RCI solution, calcium-containing plasma substitute solution. The respective compositions and contents thereof are shown as follows.

| 0.25-5.0% glutaraldehyde solution (5 L) | | | | |
|---|---|---|---|---|
| Composition | 1# | 2# | 3# | 4# |
| Magnesium sulfate | 1.0 g | 2.0 g | 3.0 g | 2.5 g |
| Potassium chloride | 3.0 g | 2.0 g | 1.0 g | 2.5 g |
| Disodium hydrogen phosphate | 3.0 g | 4.0 g | 5.0 g | 4.0 g |
| Potassium dihydrogen phosphate | 0.6 g | 1.0 g | 1.2 g | 0.8 g |
| Sodium chloride | 30.0 g | 20.0 g | 15.0 g | 25.0 g |
| 25% glutaraldehyde | 250 ml | 200 ml | 150 ml | 220 ml |
| Isopropanol | 500 ml | 700 ml | 1000 ml | 800 ml |
| Pure water | Add to 5 L | Add to 5 L | Add to 5 L | Add to 5 L |

| 0.9% saline solution (10 L) | | | | |
|---|---|---|---|---|
| Composition | 1# | 2# | 3# | 4# |
| Sodium chloride | 90 g | 90.02 g | 90.05 g | 90.06 g |
| Pure water | Add to 10 L | Add to 10 L | Add to 10 L | Add to 10 L |

| Borate buffer solution (BBS) (1 L) | | | | |
|---|---|---|---|---|
| Composition | 1# | 2# | 3# | 4# |
| Sodium chloride | 15.0 g | 10.0 g | 8.0 g | 3.0 g |
| Sodium tetraborate | 2.0 g | 3.0 g | 4.0 g | 5.0 g |
| Pure water | Add to 1 L | Add to 1 L | Add to 1 L | Add to 1 L |

| Reducing calcium ingredient (RCI) solution (1 L) | | | | |
|---|---|---|---|---|
| Composition | 1# | 2# | 3# | 4# |
| Reagent A | 150 ml | 180 ml | 300 ml | 160 ml |
| Reagent B | 30 ml | 60 ml | 10 ml | 100 ml |
| Reagent C | 0.5 g | 5 g | 9.0 g | 2.0 g |
| Solution D | 820 ml | 760 ml | 690 ml | 740 ml |

Among the above reagents:

regarding Reagent A, n-propanol is for 1#, isopropanol is for 2#, ethanol is for 3# and n-pentanol is for 4#.

regarding Reagent B, KOH is for 1# and 2#, NaOH is for 3# and 4#;

regarding Reagent C, linoleic acid is for 1#, amino oleic acid is for 2#, palmitic acid is for 3#, and oleic acid is for 4#.

reagent D is a buffer solution, phosphate buffer is for 1#, borate buffer solution is for 2# and 4#, and glycine hydrochloride buffer solution is for 3#.

| Calcium-containing plasma substitute solution (1 L) | | | | |
|---|---|---|---|---|
| Composition | 1# | 2# | 3# | 4# |
| 10% CaCl$_2$ solution | 10 ml | 12 ml | 15 ml | 13 ml |
| Hydroxyethyl starch 20 sodium chloride injection | 990 ml | 988 ml | 985 ml | 987 ml |

2. Preheat RCI Solution.

Place the RCI solution in 30-40° C. thermostat water bath for 18-24 h at a rotating speed of 5-10 rpm.

This process is mainly for preheating RCI solution, so that the active ingredients are fully uniform, to obtain a stable and effective solution for use.

3. Treatment Prior to Reducing Calcium Ingredient (PRCI).

Take valve samples, and put them into an empty container, completely soak the samples with the glutaraldehyde solution, standing for 18-24 h at room temperature.

This process is to achieve saturated cross-linking and sufficient matched functional groups of valve by soaking the valve in glutaraldehyde solution.

4. RCI Treatment.

Remove the liquid, add BBS to immerse the samples therein, clean the samples with shaking once or several times, then remove the liquid, and soak the samples in the RCI solution completely, within a 30-40° C. thermostat water bath for 67-72 h at a rotating speed of 120-130 rpm.

This process is to make the chemicals in the RCI solution chemically bond the free groups in the valve samples, to block the free aldehyde groups and carboxyl groups in the valve.

5. Valve Samples Storage.

Remove the lipid, and add 0.9% saline solution to completely soak the samples, and keep them at a temperature of 2-8° C.

6. In-Vitro Calcification Reaction.

Put the samples into the calcium-containing plasma substitute solution, thermostat water bath for 10 days, 15 days, 30 days, 60 days, at a temperature of 30-40° C., 120 rpm.

This process is an important step of evaluating the anti-calcification performance of the biological valves. The biological valves are reacted with a quantitative calcium solution sufficiently and the calcium ions are chemically bonded to the valves to evaluate the content of calcium attached to the valves.

7. Detection of Calcium Content.

The samples preserved for 0, 10, 15, 30 and 60 days were respectively taken for calcium content determination by means of atomic absorption spectrum.

| Results of calcium content detection | | | | | |
|---|---|---|---|---|---|
| | Control samples | Anti-calcification samples mg/100 g | | | |
| Days | mg/100 g | 1# | 2# | 3# | 4# |
| 0 | 13.04 | 14.15 | 16.20 | 15.25 | 15.50 |
| 10 | 31.37 | 25.44 | 22.55 | 20.36 | 21.00 |
| 15 | 48.38 | 30.95 | 28.13 | 26.83 | 27.23 |
| 30 | 98.03 | 66.78 | 62.86 | 60.59 | 61.53 |
| 60 | 236.95 | 81.40 | 78.50 | 79.20 | 78.60 |

As can be seen from the results of the above table, the calcium content of the samples after RCI processing is lower than that of the control samples, and the evaluation method is shown to be effective.

The method for in-vitro biological valve calcification evaluation according to the present invention greatly shortens the calcification evaluation period, compared with the 6 months for animal clinical, it has been shortened by 4 months. In the meanwhile, the procedures have been reduced, the participation of experimental animals and clinicians are no longer required, which greatly saves the cost of research. Calcification evaluation of biological valve by treated chemically, formed an efficient evaluation method, standardized evaluation method, which is less susceptible to other factors, of positive evaluation significance of biological valve calcification caused by chemical groups, and also plays a role in assisting and guiding the subsequent calcification evaluation of biological valves within animals.

It should be understood that the above embodiments are merely intended to describe the technical solutions of the present invention rather than limiting the present invention. For those skilled in the art, the technical solutions described in the foregoing embodiments may be modified or some technical features may be replaced with equivalents, and all the modifications and replacements shall be encompassed in the scope of the appended claims of the present invention.

What is claimed is:

1. An in-vitro biological valve calcification evaluation method, comprising the steps of:
   (1) preparing calcification evaluation solutions, the calcification evaluation solutions comprising: glutaraldehyde solution, saline solution, borate buffer solution, reducing calcium ingredient solution and calcium-containing plasma solution, wherein the reducing calcium ingredient solution comprises an alcohol, an alkaline solution, an oil and/or its derivatives, and a buffer solution;
   (2) preheating the reducing calcium ingredient solution by placing the reducing calcium ingredient solution in a 30 to 40° C. thermostat water bath;

(3) conducting treatment prior to reducing calcium ingredient solution by taking a biological valve sample and soaking the biological valve sample in the glutaraldehyde solution completely, and maintaining the biological valve sample at room temperature;

(4) conducting treatment with the reducing calcium ingredient solution by removing the glutaraldehyde solution, and adding the borate buffer solution, immersing the sample therein, then removing the borate buffer solution, and soaking the sample in the reducing calcium ingredient solution completely within a 30 to 40° C. thermostat water bath;

(5) preserving the biological valve samples by removing the reducing calcium ingredient solution from a container and adding the saline solution until the biological valve sample is completely soaked, and storing the sample in the container;

(6) conducting an in-vitro calcification reaction by putting the biological valve sample into the calcium-containing plasma solution in a 30 to 40° C. thermostat water bath for a period of any days within 60 days to let the biological valve sample fully react with the given calcium ions of the solution, such that calcium ions are bonded to the biological valve sample by chemical bonding ;

(7) detecting calcium content measuring the calcium content of the biological reacted valve sample by atomic absorption spectrometry to evaluate the calcium content of the biological valve sample, and comparing it with a standard sample.

2. The in-vitro biological valve calcification evaluation method according to claim 1, wherein the concentration of the glutaraldehyde solution is from 0.25% to 5.0% and compositions and contents of each 5 L volume of the glutaraldehyde solution comprises: 1.0 to 3.0 g of magnesium sulfate; 1.0 to 3.0 g of potassium chloride; 3.0 to 5.0 g of disodium hydrogen phosphate; 0.6 to 1.2 g of potassium dihydrogen phosphate; 15 to 30 g of sodium chloride; 150 to 250 ml of 25% glutaraldehyde; 500 to 1000 ml of isopropanol; and pure water to complete to 5 L total volume.

3. The in-vitro biological valve calcification evaluation method according to claim 1, wherein the concentration of the saline solution is 0.9%, the compositions and contents of each 10 L volume of the saline solution comprises: 90 g±0.1 g of sodium chloride; and pure water to complete to 10 L total volume.

4. The in-vitro biological valve calcification evaluation method according to claim 1, wherein the compositions and contents of each 1 L volume of the borate buffer solution comprises: 3.0 to 15.0 g of sodium chloride; 2.0 to 5.0 g of sodium tetraborate; and pure water to complete to 1 L total volume, with a pH of 8.5 to 9.5.

5. The in-vitro biological valve calcification evaluation method according to claim 1, wherein the compositions and contents of each 1 L volume of the reducing calcium ingredient solution comprises: 150 to 300 ml of reagent A, wherein reagent A is an alcohol; 10 to 100 ml of reagent B, wherein reagent B is an alkaline solution; 0.5 to 9.0 g of reagent C, wherein-the reagent C is an oil or a derivative thereof; 690 to 820 ml of reagent D with a pH of 8.5 to 9.5, wherein reagent D is a buffer solution.

6. The in-vitro biological valve calcification evaluation method according to claim 1, wherein the calcium-containing plasma is a plasma substitute, the compositions and contents of each 1 L volume of the calcium-containing plasma comprises: 10 to 15 ml of 10% $CaCl_2$ solution; and 900 to 1000 ml of hydroxyethyl starch sodium chloride injection.

7. The in-vitro biological valve calcification evaluation method according to claim 5, wherein reagent A comprises any one of ethanol, isopropanol, and amyl alcohol.

8. The in-vitro biological valve calcification evaluation method according to claim 5, wherein reagent B comprises KOH or NaOH.

9. The in-vitro biological valve calcification evaluation method according to claim 5, wherein reagent C comprises one or more of tetraenoic acid, linoleic acid, eicosatrienoic acid, linolenic acid, aminoleic acid, lauric acid, heptanoic acid, palmitic acid, stearic acid, oleic acid, and derivatives thereof.

10. The in-vitro biological valve calcification evaluation method according to claim 5, wherein reagent D is buffer solution comprising phosphate buffer solution, borate buffer solution or glycine hydrochloride buffer solution.

11. A reducing calcium ingredient solution, comprising:
reagent A;
reagent B;
reagent C; and
reagent D,
wherein reagent A is an alcohol, comprising any one of ethanol, isopropanol and amyl alcohol; reagent B is an alkaline solution, comprising KOH or NaOH; reagent C is an oil and/or its derivatives, comprising one or more of tetraenoic acid, linoleic acid, eicosatrienoic acid, linolenic acid, aminoleic acid, lauric acid, heptanoic acid, palmitic acid, stearic acid, and derivatives thereof; and reagent D is a buffer solution with a PH of 8.5 to 9.0 comprising phosphate buffer, borate buffer or glycine hydrochloride buffer.

\* \* \* \* \*